(12) United States Patent
Abraham et al.

(10) Patent No.: US 9,241,839 B2
(45) Date of Patent: Jan. 26, 2016

(54) ABSORBENT ARTICLE FULLNESS INDICATOR

(75) Inventors: Jose Kollakompil Abraham, Neenah, WI (US); Thomas Michael Ales, III, Neenah, WI (US); Sudhanshu Gakhar, Neenah, WI (US); Jeffrey Robert Heller, Neenah, WI (US); Davis Dang Hoang Nhan, Appleton, WI (US); Joseph Raymond Feldkamp, Appleton, WI (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 958 days.

(21) Appl. No.: 13/183,811

(22) Filed: Jul. 15, 2011

(65) Prior Publication Data

US 2013/0018340 A1    Jan. 17, 2013

(51) Int. Cl.
*A61F 13/42* (2006.01)

(52) U.S. Cl.
CPC ..................... *A61F 13/42* (2013.01)

(58) Field of Classification Search
USPC .......................................... 604/361
See application file for complete search history.

(56) References Cited

U.S. PATENT DOCUMENTS

| | | | |
|---|---|---|---|
| 5,463,377 A * | 10/1995 | Kronberg | 340/605 |
| 5,469,145 A * | 11/1995 | Johnson | 340/604 |
| 5,568,128 A | 10/1996 | Nair | |
| 5,760,694 A * | 6/1998 | Nissim et al. | 340/604 |
| 5,868,723 A * | 2/1999 | Al-Sabah | 604/361 |
| 5,903,222 A | 5/1999 | Kawarizadeh et al. | |
| 6,186,991 B1 * | 2/2001 | Roe et al. | 604/361 |
| 6,200,250 B1 | 3/2001 | Janszen | |
| 6,774,800 B2 * | 8/2004 | Friedman et al. | 340/573.5 |
| 7,141,715 B2 * | 11/2006 | Shapira | 604/361 |
| 7,355,090 B2 * | 4/2008 | Ales, III et al. | 604/361 |
| 7,855,653 B2 * | 12/2010 | Rondoni et al. | 340/573.5 |
| 2004/0036484 A1 | 2/2004 | Tamai | |
| 2004/0064114 A1 * | 4/2004 | David et al. | 604/361 |
| 2004/0138633 A1 * | 7/2004 | Mishima et al. | 604/361 |
| 2004/0207530 A1 | 10/2004 | Nielsen | |
| 2004/0220538 A1 * | 11/2004 | Panopoulos | 604/361 |
| 2005/0033250 A1 | 2/2005 | Collette et al. | |
| 2005/0195085 A1 | 9/2005 | Cretu-Petra | |
| 2007/0049881 A1 | 3/2007 | Ales et al. | |
| 2007/0142797 A1 | 6/2007 | Long et al. | |
| 2007/0142799 A1 * | 6/2007 | Ales et al. | 604/361 |
| 2007/0270774 A1 * | 11/2007 | Bergman et al. | 604/361 |

(Continued)

FOREIGN PATENT DOCUMENTS

| | | |
|---|---|---|
| CN | 201267570 Y | 8/2008 |
| JP | 2007-143994 A | 6/2007 |

(Continued)

*Primary Examiner* — Susan Su
(74) *Attorney, Agent, or Firm* — Kimberly-Clark Worldwide, Inc.

(57) ABSTRACT

A wetness monitoring system is provided for an absorbent article, the wetness monitoring system including a signaling device including an alarm to indicate that the absorbent article has reached an insult limit. The signaling device operates with a sensor array which is disposed on the outermost surface of the absorbent article outer cover. The signaling device includes a detection circuit which measures changes in inductance or capacitance. The wetness monitoring system does not make direct contact with the absorbent structure located within an outer cover of the absorbent article.

21 Claims, 14 Drawing Sheets

(56) References Cited

U.S. PATENT DOCUMENTS

| | | |
|---|---|---|
| 2008/0058740 A1* | 3/2008 | Sullivan et al. ............... 604/361 |
| 2008/0058743 A1* | 3/2008 | Cohen et al. .................. 604/361 |
| 2008/0086103 A1* | 4/2008 | McKiernan et al. ..... 604/385.02 |
| 2008/0147031 A1 | 6/2008 | Long et al. |
| 2008/0278337 A1 | 11/2008 | Huang et al. |
| 2008/0300559 A1* | 12/2008 | Gustafson et al. ............ 604/361 |
| 2009/0005748 A1* | 1/2009 | Ales et al. .................... 604/361 |
| 2009/0124990 A1* | 5/2009 | Feldkamp et al. ............ 604/361 |
| 2010/0114046 A1* | 5/2010 | Ales et al. .................... 604/361 |
| 2010/0164733 A1 | 7/2010 | Ales et al. |
| 2010/0168702 A1* | 7/2010 | Ales et al. .................... 604/361 |

FOREIGN PATENT DOCUMENTS

| | | |
|---|---|---|
| KR | 100950864 B1 | 7/2009 |
| WO | WO 2006/134940 A1 | 12/2006 |
| WO | WO 2009/063358 A2 | 5/2009 |
| WO | WO 2010/012217 A1 | 2/2010 |
| WO | WO 2010/049827 A2 | 5/2010 |
| WO | WO 2011/013874 A1 | 2/2011 |

\* cited by examiner

ABSORBENT ARTICLE FULLNESS INDICATOR

BACKGROUND

The present invention relates generally to a system and method of detecting the amount of liquid in an absorbent article while it is being worn by a wearer and for alerting the wearer or a caregiver to the fullness status.

An absorbent article containing a superabsorbent material is typically capable of holding more than an average urine insult from a wearer such as a baby or an incontinent adult. Thus, users often will not change the absorbent article until it contains a bowel movement or the absorbent article feels saturated with urine. Wetness indicators have been developed so that users can know when an insult has occurred.

Absorbent articles associated with wetness indicators provide a signal to a user when the absorbent article has been insulted. The indicators send an electrical signal to a device that transmits visible, vibratory and/or audible notice that an insult has occurred. Typically, a pair of spaced-apart parallel conductors is situated within the absorbent material of the undergarment. These conductors are in electrical contact with the absorbent material of the undergarment and are connected to a sensing circuit for monitoring the electrical property.

When absorbent articles include a wetness indicator with conductors that are in electrical contact with the absorbent material of the undergarment, the machine line on which the absorbent articles are made is altered in the portion of the line where the article's absorbent structure is made. This is disruptive to the manufacturing process. Further, incorporating conductive leads in an absorbent core at conventional manufacturing speeds has been problematic.

In addition to challenges associated with the manufacture of absorbent articles with electrodes incorporated in the absorbent article, the user may desire to know not only that the absorbent article is wet, but the level of wetness. Without knowing whether the absorbent is near to or has reached saturation, one may change the article prematurely.

SUMMARY

Disclosed is a system that allows a caregiver or wearer to determine when an absorbent article should be changed based on a predetermined wetness level, and a solution to the manufacturing challenges mentioned herein. More specifically, this is a disclosure of a system that allows a caregiver or wearer to know how wet an article's absorbent structure is after having been insulted numerous times. The system does not require any modifications to the absorbent article manufacturing line Instead, the user or caregiver has the option to place the system 100 on a conventional absorbent garment.

One aspect of the disclosure is a system for sensing and indicating the presence of a body exudate in an absorbent article. The system includes a signaling device having a housing which houses a detection circuit, and a sensor array electrically connected to the detection circuit. The sensor array includes a plurality of sensors disposed on an elongated substrate.

Another aspect of the disclosure is a wetness detection kit. The kit includes a plurality of absorbent articles and a system for sensing and indicating the presence of a body exudate in an absorbent article. The system includes a signaling device having a housing and a detection circuit, and a sensor array electrically connected to the detection circuit. The sensor array has a plurality of sensors disposed on an elongated substrate. The system may be sequentially and removably attached to each one of the plurality of absorbent articles.

Yet another aspect of the disclosure is a body exudate collection and detection system having an absorbent article and a signaling device. The signaling device includes a housing and a detection circuit. The sensor array is electrically connected to the detection circuit and partially housed by the housing, wherein the sensor array has a plurality of sensors disposed on an elongated substrate. The system is attached to the outer cover of the absorbent article.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings.

Figure 1:
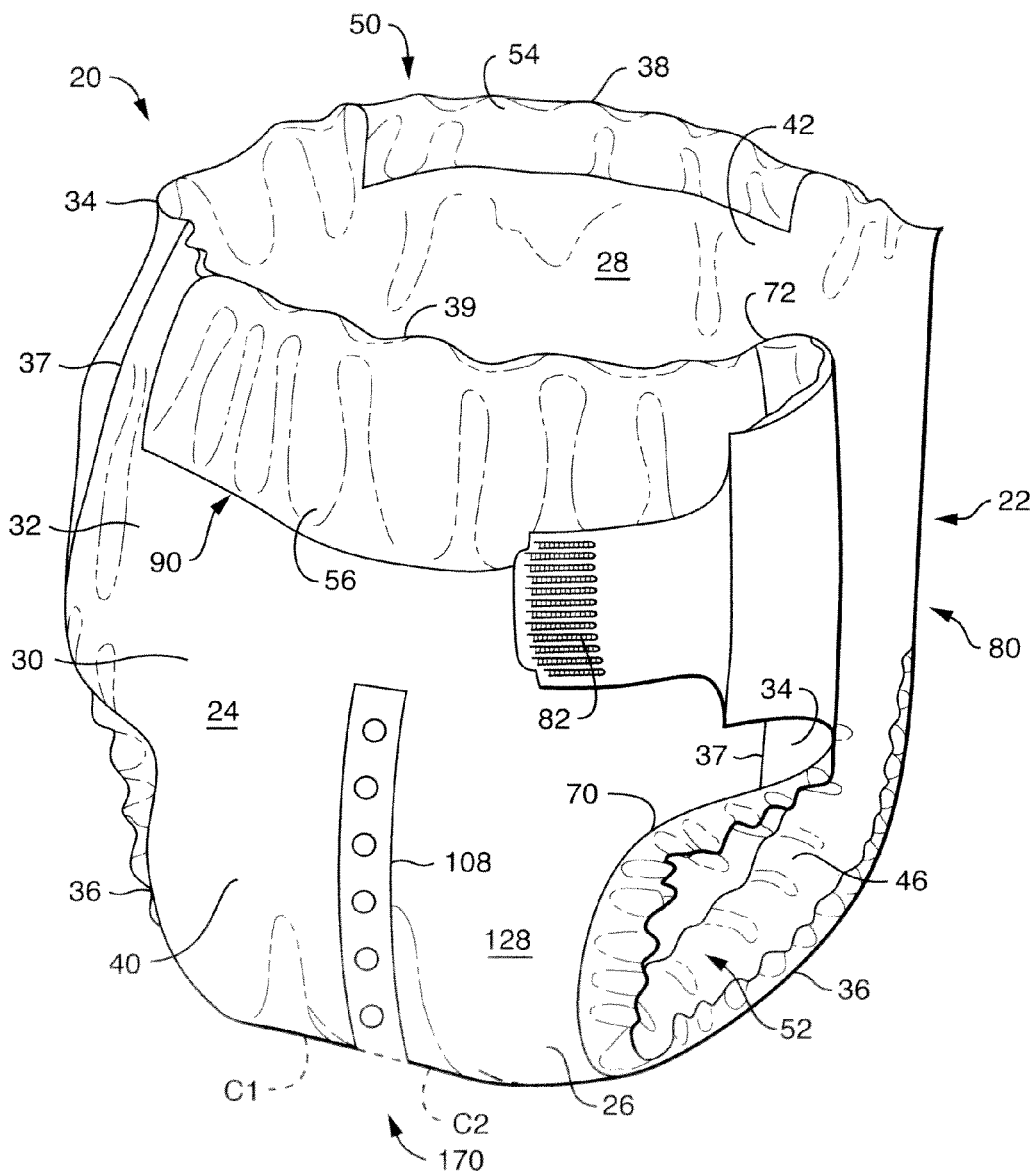
FIG. 1 is a rear perspective view of one aspect of an absorbent article.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary aspects only, and is not intended as limiting the broader aspects of the present disclosure.

Newborns and infants exhibit urination patterns that are different from those of children who are potty training. Newborns and infants will often insult a product 20 mL at a time with only minutes, such as 10-20 minutes, between urinations. Similar behavior can be displayed by users of adult incontinence products as well. To determine when the absorbent article has or is soon to be saturated, a wetness sensing system is used. This system can be enabled with higher order algorithms to collect and process electrical data captured from the absorbent article when the absorbent article and wetness sensing device are in use.

As used herein, the terms wearer, adult or infant refer to the subject who has donned the absorbent article. Caregiver refers to a person who is taking care of the adult or infant, including changing the absorbent article. User can refer to either the caregiver or the wearer of the absorbent article, depending on the context of its use and the capabilities needed to use the object in question.

Figure 2:
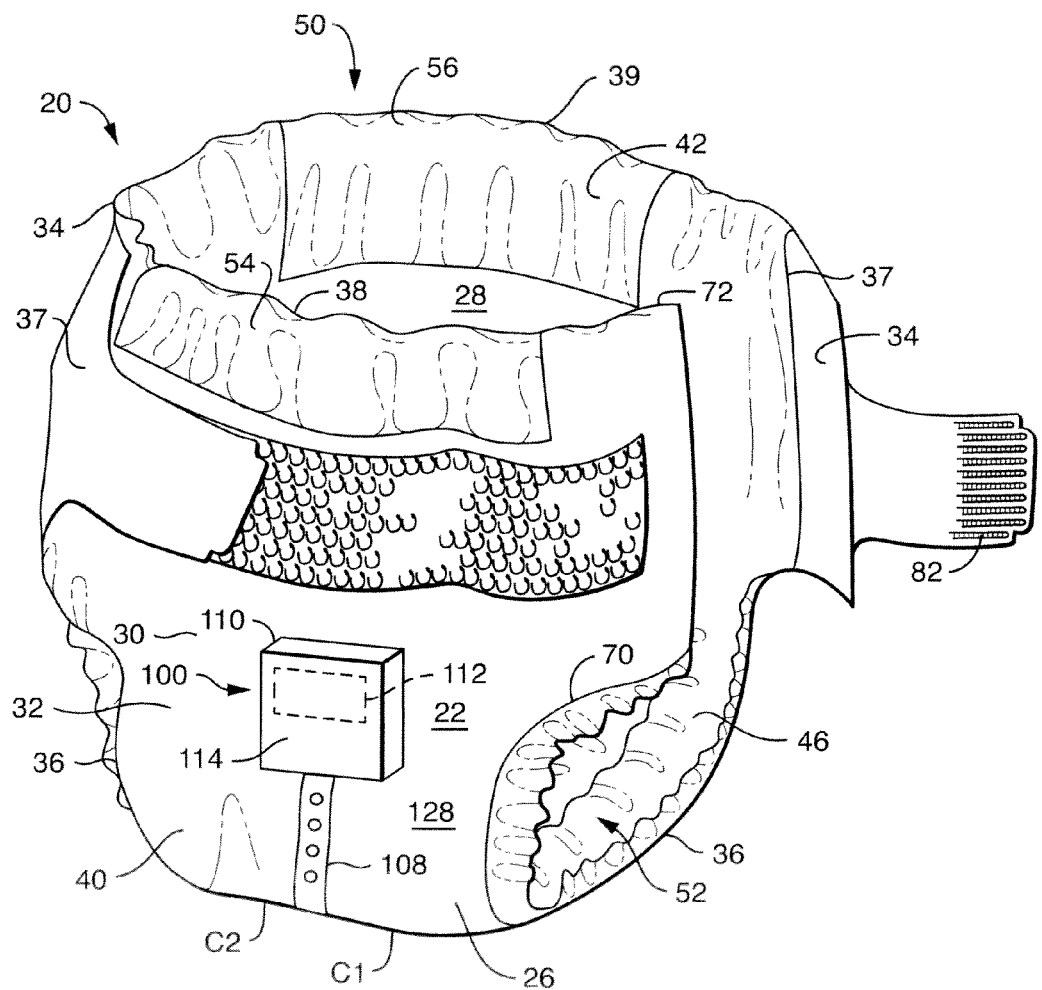
FIG. 2 is a front perspective view of the absorbent article illustrated in FIG. 1.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other absorbent articles intended for personal wear including, but not limited to, diapers, training pants, swim pants, feminine hygiene products, incontinence products, medical garments, surgical pads and bandages, other personal care or health care garments, and the like, without departing from the scope of the present disclosure.

By way of illustration only, various materials and methods for constructing absorbent articles such as the diaper 20 of the various aspects of the present disclosure are disclosed in PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
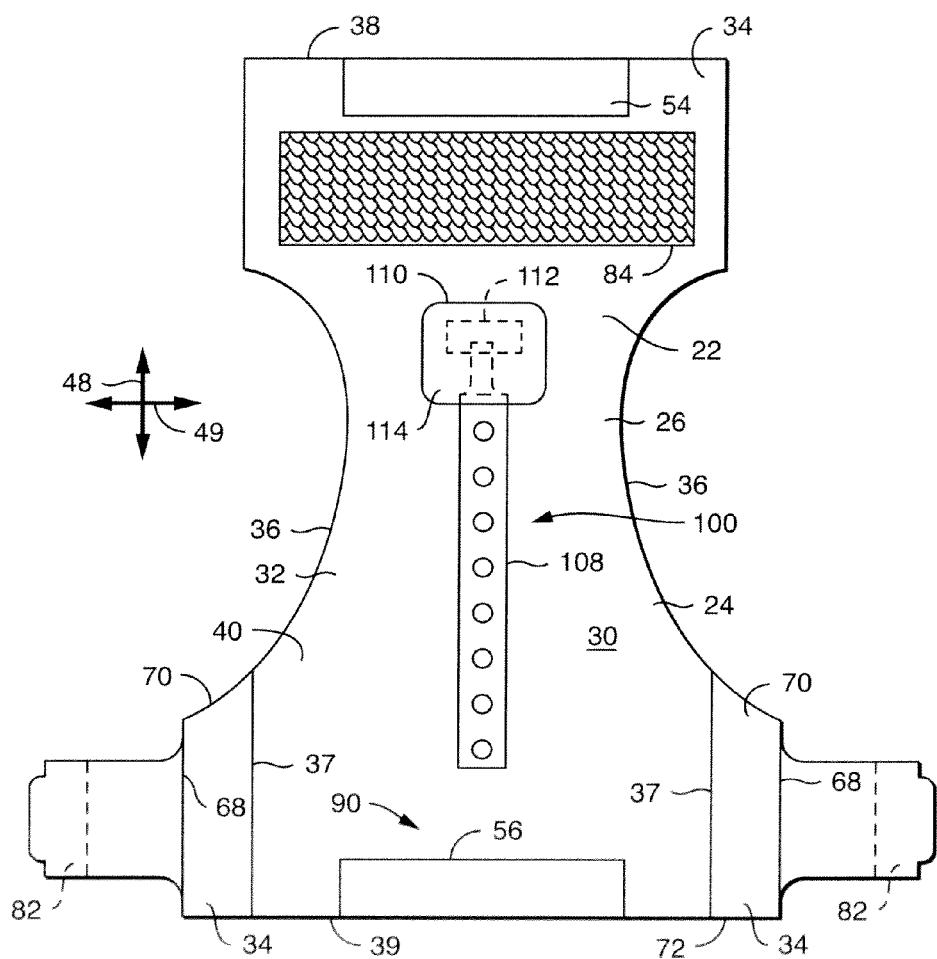
FIG. 3 is a plan view of the absorbent article shown in FIG. 1 with the article in an unfastened, unfolded and laid flat condition showing the surface of the article that faces away from the wearer.
Figure 4:
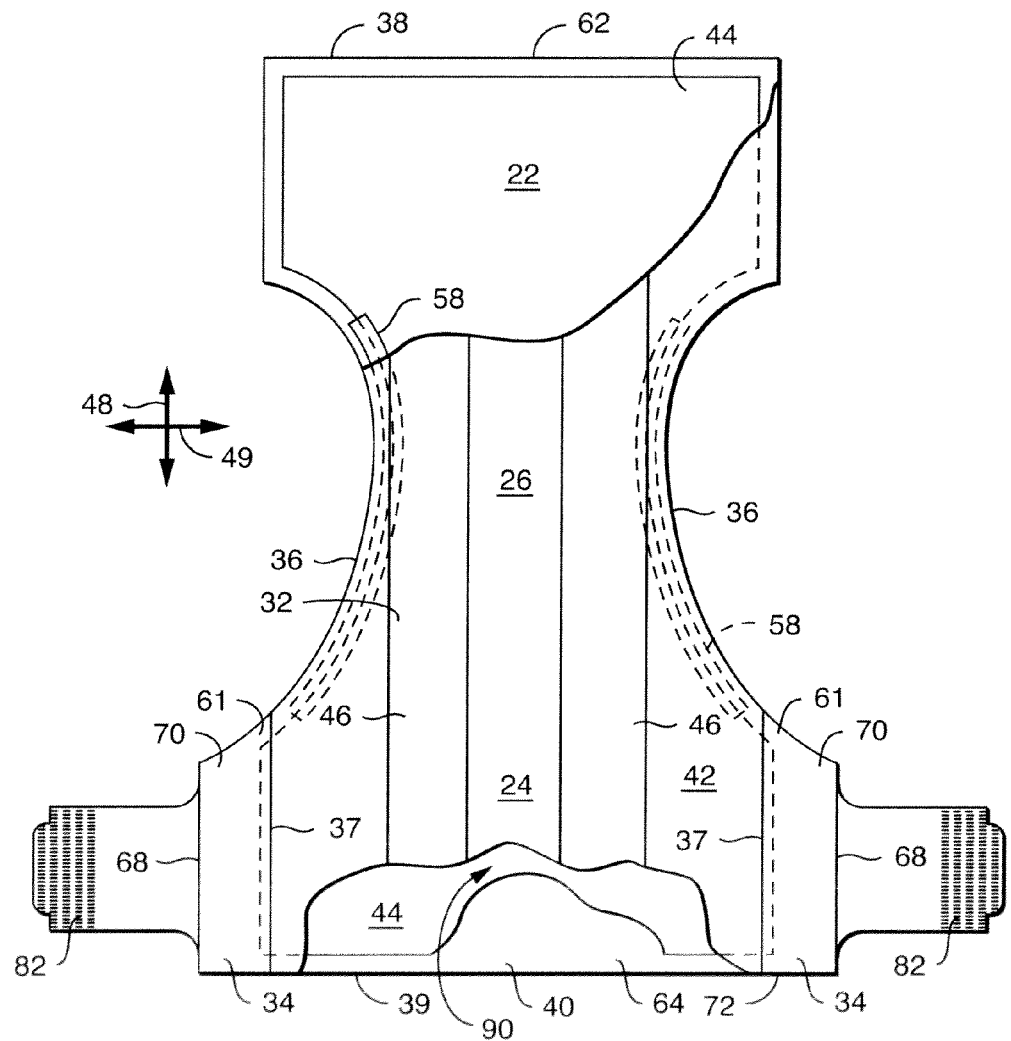
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface 28. The front and back regions 22, 24 are those portions of the diaper 20 which, when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearers body. The containment flaps 46 can extend longitudinally along the entire length of the chassis 32 or may extend only partially along the length of the chassis 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some aspects, the absorbent article 20 may further include a surge management layer 60 that may be optionally located adjacent the absorbent structure 44 and attached to various components in the article 20, such as the absorbent structure 44 or the bodyside liner 42, by methods known in the art, such as by using an adhesive. A surge management layer 60 helps to decelerate and diffuse surges or gushes of liquid that may be rapidly introduced into the absorbent structure 44 of the article 20. Desirably, the surge management layer 60 can rapidly accept and temporarily hold the liquid prior to releasing the liquid into the storage or retention portions of the absorbent structure 44. Examples of suitable surge management layers 60 are described in U.S. Pat. No. 5,486,166 issued Jan. 23, 1996 to David F. Bishop et al. and U.S. Pat. No. 5,490,846 issued Feb. 13, 1996 to Clifford J. Ellis et al. Other suitable surge management materials are described in U.S. Pat. No. 5,820,973 issued Oct. 13, 1998 to Richard N. Dodge II et al. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels 34 are attached to the chassis 32 along a pair of opposing longitudinal edges 37. The side panels 34 may be attached or bonded to the chassis 32 using any suitable bonding technique. For instance, the side panels 34 may be joined to the chassis 32 by adhesives, ultrasonic bonds, thermal bonds, or other conventional techniques.

In an alternative aspect, the elastic side panels 34 may also be integrally formed with the chassis 32. For instance, the side panels 34 may comprise an extension of the bodyside liner 42, of the outer cover 40, or of both the bodyside liner 42 and the outer cover 40.

In the aspects shown in the figures, the side panels 34 are connected to the back region 24 of the absorbent article 20 and extend over the front region 22 of the article 20 when securing the article 20 in place on a user. It should be understood, however, that the side panels 34 may alternatively be connected to the front region 22 of the article 20 and extend over the back region 24 when the article 20 is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the aspects shown in the figures, the side panels 34 are releasably attachable to the front region 22 of the article 20 by the fastening system 80. It should be understood, however, that in other aspects, the side panels 34 may be permanently joined to the chassis 32 at each end. The side panels 34 may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article 20. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge 70 of the back region 24, or alternatively, neither of the leg end edges 70 may be curved or angled, without departing from the scope of the present disclosure. As shown in FIG. 4, the outer edges 68 are generally parallel to the longitudinal direction 48 while the waist end edges 72 are generally parallel to the lateral direction 49. It should be understood, however, that in other aspects the outer edges 68 and/or the waist edges 72 may be slanted or curved as desired. Ultimately, the side panels 34 are generally aligned with a waist region 90 of the chassis 32.

The fastening system 80 may include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 include a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material, or the like. One skilled in the art will recognize that the shape, density, and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the aspect shown in the figures, the fastening components 82 are attached to the side panels 34 along the edges 68. In this aspect, the fastening components 82 are not elastic or extendable. In other aspects, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening 50. For example, as shown in the figures, the absorbent article 20 can include a front waist elastic member 54 and/or a back waist elastic member 56.

The materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded-carded webs or foams provided by elastomeric or polymeric materials. The outer cover 40, for instance, can be a single layer of a liquid impermeable material, or alternatively can be a multi-layered laminate structure in which at least one of the layers is liquid impermeable. In other aspects, however, it should be understood that the outer cover 40 may be liquid permeable. In this aspect, for instance, the absorbent article 20 may contain an interior liquid barrier layer.

For instance, the outer cover 40 can include a liquid permeable outer layer and a liquid impermeable inner layer that are suitably joined together by a laminate, adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40, when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearers skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., U.S.A., and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air-forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394 and Favor 9543 superabsorbents are available from DeGussa Superabsorbers, located at Parsippany, N.J., U.S.A.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

Figure 11:
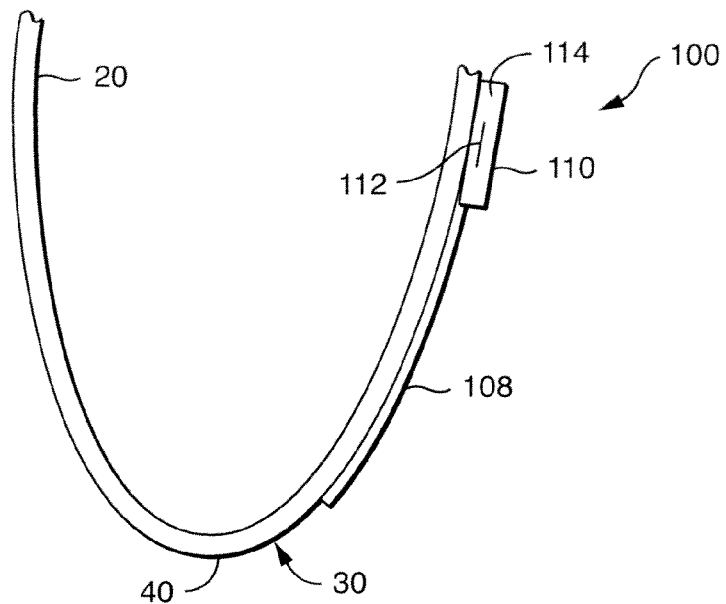
FIG. 11 is a side cross-section of an absorbent garment according to one aspect of the disclosure onto which a display and related sensors are disposed.
Figure 12:
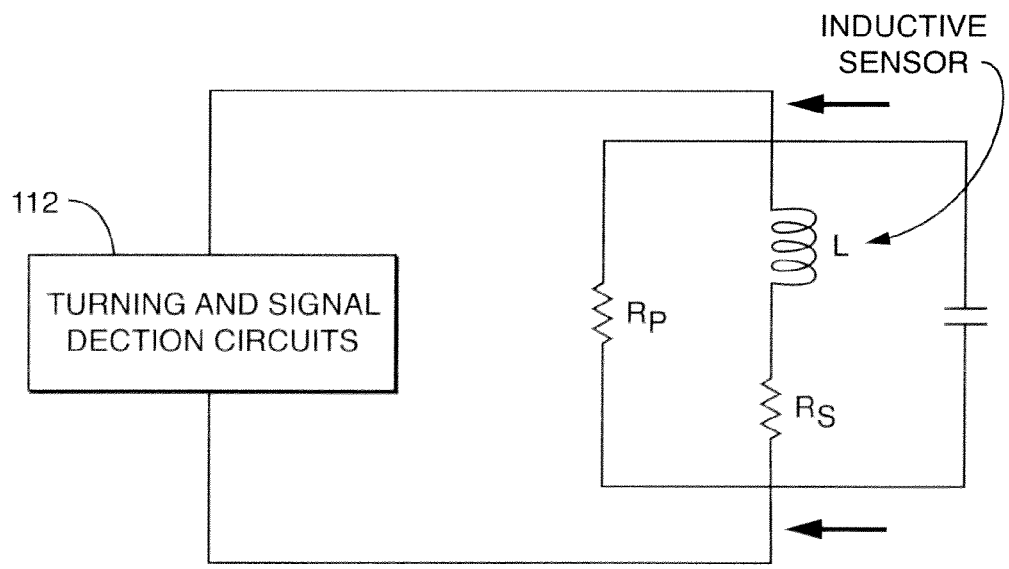
FIG. 12 is one aspect of a schematic of a circuit having an inductive sensor according to one aspect of the disclosure.

Shown in FIGS. 3 and 11 is one example of the wetness monitoring system generally indicated by reference numeral 100. The monitoring system 100 includes a sensor array 108 and a signaling device 110 having a detection circuit 112. The detection circuit 112 detects an electrical property (e.g., inductance or capacitance) of the article 20. When a body exudate is present in the absorbent article 20, the detection circuit 112 detects the presence of the body exudate and activates the signaling device 110. The monitoring system 100 has no physical contact with the diaper interior inside the outer cover 40. Thus, the system 100 is disposed onto the outermost surface of the outer cover 40.

The complete detection circuit 112 is disposed in a housing 114 (see FIGS. 2 and 3) that is adapted to be attached to the absorbent article 20 along with sensor array 108. The housing 114 can be a pouch or a rigid or semi-rigid housing 114. Additional technical detail is provided in co-pending and co-assigned U.S. patent application Ser. No. 12/968,399 filed on Dec. 15, 2010, by Nhan et al., and incorporated herein by reference to the extent it is consistent (i.e., not in conflict) herewith.

An attachment mechanism that can be used to attach the system 100 to the outer cover 40 of the absorbent article 20 includes adhesive, hook and loop, mechanical fasteners such as snaps, a clip, or a clasp, any other suitable attachment mechanism, or any combination of these fasteners. Various attachment mechanisms include those disclosed in co-pending and co-assigned U.S. Patent Application Publication No. 2007/0142797 to Long, et al. and entitled "Garments With Easy-To-Use Signaling Device"; U.S. Pat. No. 7,394,391 issued to Long and entitled "Connection Mechanisms"; and U.S. Pat. No. 7,477,156 issued to Long, et al. and entitled "Connection Mechanisms In Absorbent Articles For Body Fluid Signaling Devices" which are incorporated herein by reference to the extent they are consistent (i.e., not in conflict) herewith.

The sensor array 108 is affixed to the outermost surface of the outer cover 40. The sensor array 108 is oriented in the longitudinal direction 48 and may extend longitudinally from the front region 22, through the crotch region 26, to the back region 24 of the absorbent article 20. However, the sensor array 108 may be located only on a portion of these regions such as on the front region 22 as depicted in FIG. 1.

Because the sensor array 108 is attached to the outer cover 40 and can monitor the status of the article 20 interior without making direct contact with the absorbent structure 44, the manufacture of the absorbent article 20 is simplified. Generally, this arrangement allows the addition of a sensor array 108 to an absorbent article 20 without having to make any manufacturing process modifications to the article 20.

In some aspects of the present disclosure, the signaling device 110 can include a display of the number of insults, a display of the elapsed time, a percentage of fullness, or a combination thereof. When the signaling device 110 issues a visible signal, the visible signal may comprise one light, multiple lights, or an interactive display. The lights may be an LCD display, a series of LED lights, or any other display type suitable for displaying such information to a user. In other aspects of the present disclosure, the signaling device 110 can be configured to vibrate.

The signaling device 110 can include a transmitter and a receiver (not shown). In particular, in one aspect of the present disclosure, the transmitter sends a wireless signal to the receiver which then indicates to a wearer or caregiver that a body exudate is present in the absorbent article 20. Further details on this aspect can be obtained in, for example, in U.S. Pat. No. 7,394,391 issued to Long and entitled "Connection Mechanisms," which is incorporated herein by reference to the extent it is consistent (i.e., not in conflict) herewith.

Figure 15:
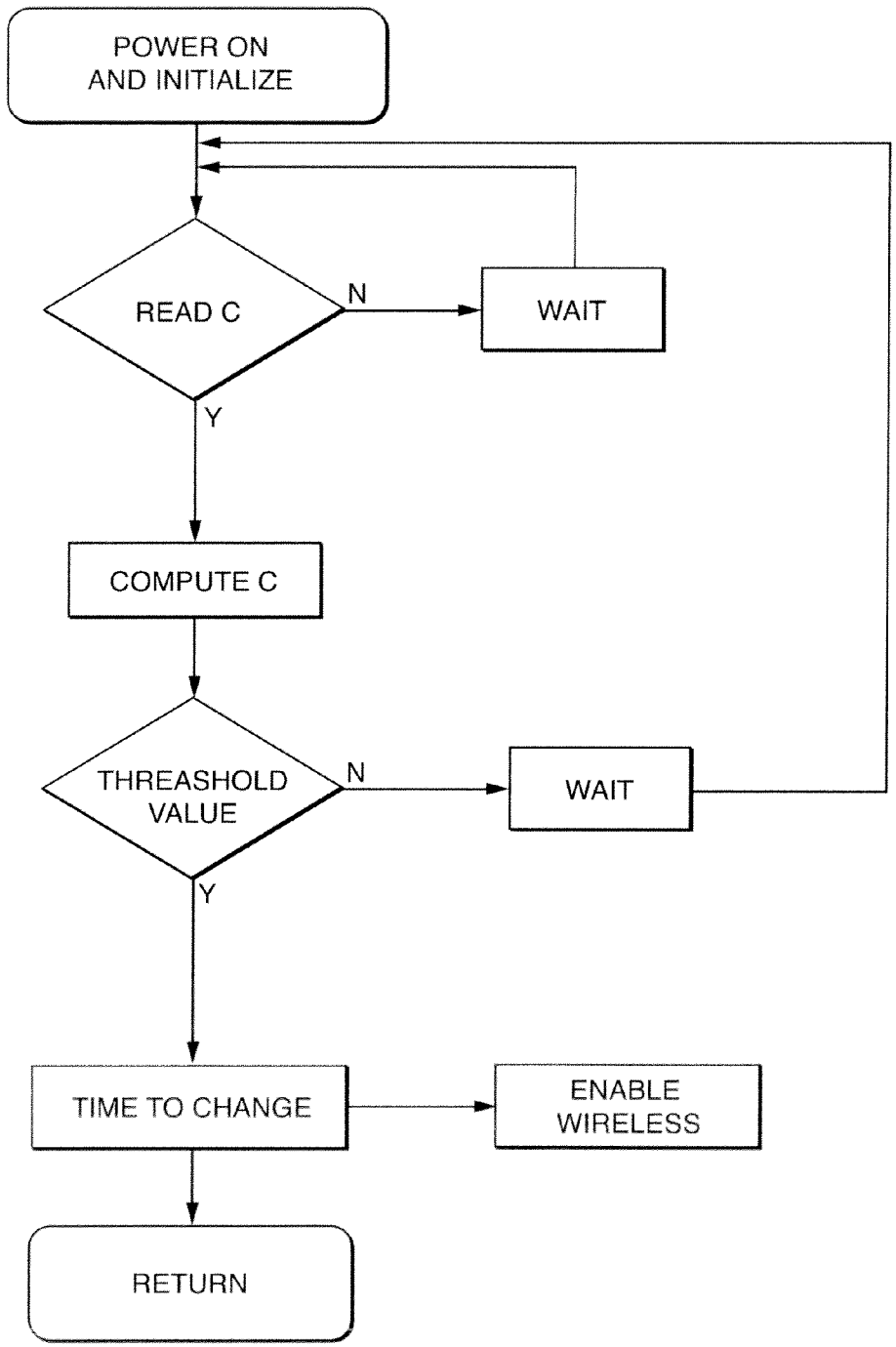
FIG. 15 is a flow chart showing one aspect of an algorithm for using capacitance data to determine when an absorbent article has reached a desired or predetermined level of wetness.
Figure 16:
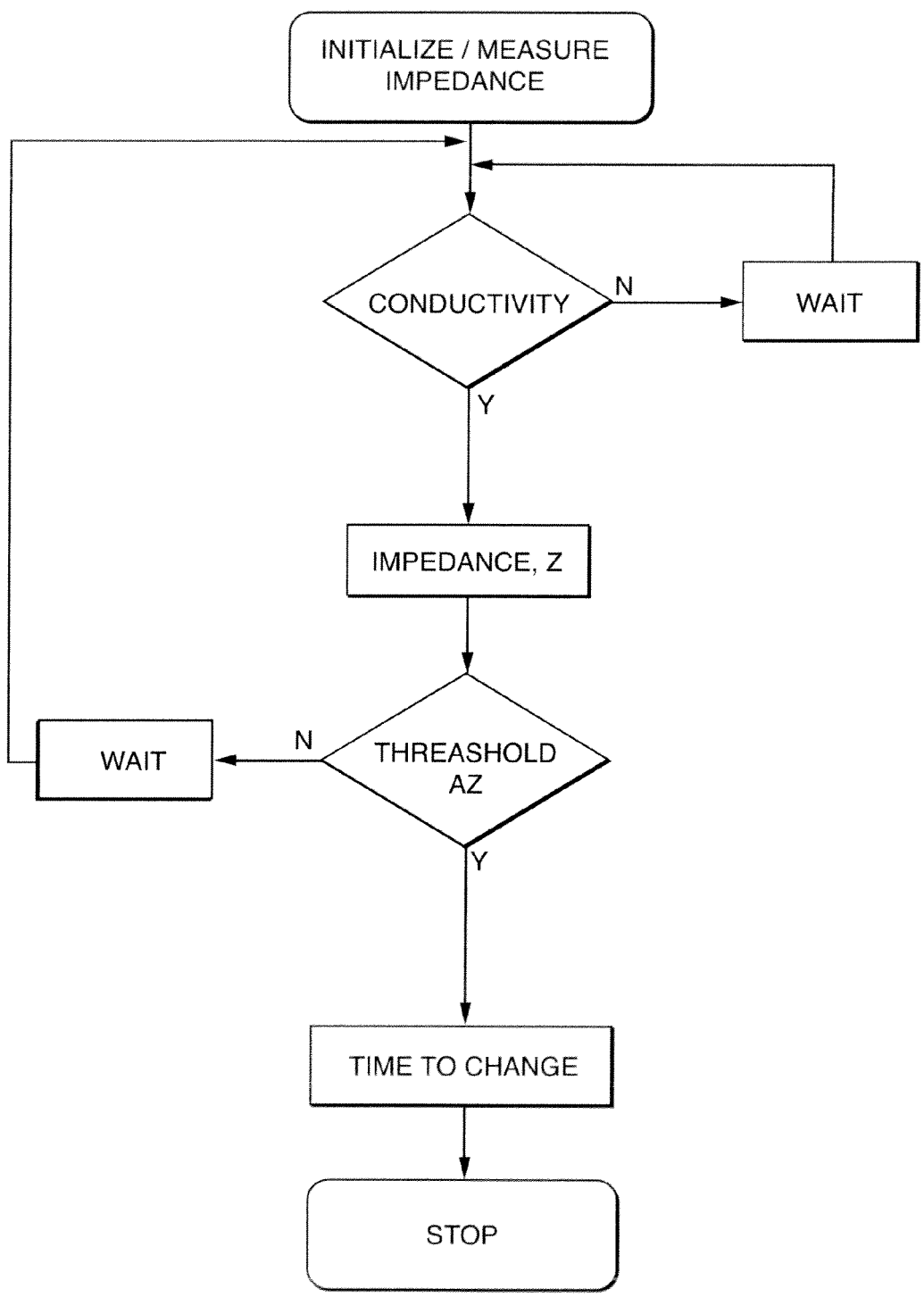
FIG. 16 is a flow chart showing one aspect of an algorithm for using inductance data to determine when an absorbent article has reached a desired or predetermined level of wetness.

The signaling device 110, when connected to or placed in the proximity of absorbent article 20, collects electrical data which can be obtained by capacitive or inductive means as described herein. The data is used in an algorithm that determines when the absorbent article 20 has reached a predetermined level of fullness. FIGS. 15 and 16 provide an exemplary illustration of such an algorithm, discussed herein.

In one aspect of the disclosure, the sensor array 108 is defined by an inductor array 122 disposed on the outer cover 40 of absorbent article 20. Together, the inductors 124 of the array measures the physical property of the absorbent article 20 by measuring conductivity within the monitoring area 128. The conductivity directly correlates with the absorbency and hence the saturation level of the absorbent structure 44. Additional technical details regarding the conductive elements and specific electronic pulsing and signaling analysis is provided in co-pending and co-assigned U.S. Patent Application Publication No. 2010/0114046 filed on Oct. 30, 2008, by Ales et al.

The detection circuit 112 monitors changes in impedance in response to bodily waste in the proximity of a monitoring area 128. Monitoring area 128 is the region of the absorbent article 20 that is within the proximity of the inductor array 122. The inductor array 122 includes one or more induction coils 125 that, when placed in the vicinity of a conductive liquid such as urine, will generate weak electrical eddy currents in the liquid. The electrical currents in turn generate a field that couples with the induction coil 125, changing its impedance.

The inductor array 122 can be fabricated using printed circuit fabrication techniques on a flexible substrate. For example, conducting inks may be printed on a flexible plastic sheet. The typical inductor shape is circular. However, rectangular, square, triangle or any other inductor shapes can be used.

Induction coils 125 can be made as small as having a diameter of about 1.0 mm, although the field of view of the induction coil 125 is reduced as the diameter of the coil 125 is reduced. Induction coils 125 can also be made large to increase the field of view, with diameters as large as 8 cm, but larger induction coils 125 can become impractical for use with absorbent article applications. Although induction coils 125 of any size can be used, coils 125 in the range of about 0.5 cm to about 3 cm are more practical. Likewise, coils 125 in the range of about 1 cm to about 2 cm have additional advantages. Finally, coils 125 in the range of about 1 cm to about 1.5 cm have the most practicality.

Figure 17:
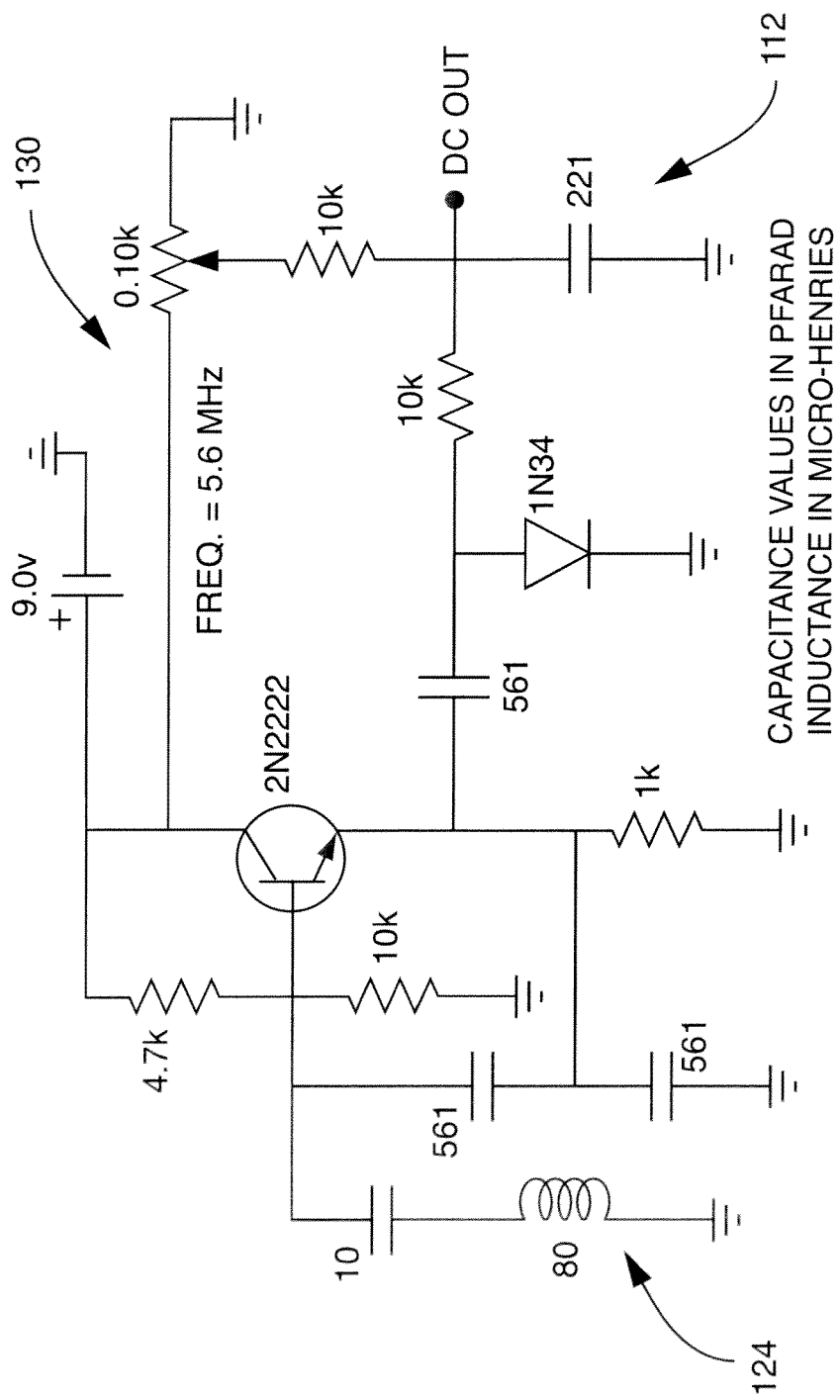
FIG. 17 is a schematic of one aspect of the disclosure including an induction coil and a marginal oscillator.

The detection circuit 112 includes a marginal oscillator circuit 130. The marginal oscillator circuit 130 is used to detect the altered impedance of the induction coil 125. An example of such an oscillator circuit 130 is illustrated in FIG. 17. The marginal oscillator circuit 130, in its simplest form, is a standard Colpitts-type oscillator that has just barely enough feedback to drive it into oscillation. In other aspects of the present application, the oscillator can be any suitable oscillator circuit including a Franklin or a Hartley oscillator. When conductive objects are brought close to the induction coil 125, energy is removed from the oscillator due to ohmic losses in the conductive object. This removal of energy registers in the oscillator's output, which in this case can be interpreted to measure either the amount of conductive liquid in the absorbent article or the liquid's conductivity. Once the signaling device 110 is activated, the processor takes a baseline measurement, which is automatic and transparent to the user. The detection circuit 112 automatically zeroes itself to establish the point of zero wetness baseline needed.

The electronics associated with the detection circuit 112 are relatively simple and can be miniaturized to postage stamp size. The detection circuit 112 includes the induction coil 125, which in one example includes about 40 turns of #36 copper wire formed into a planar loop about 2 cm in diameter.

Figures 10A, 10B:
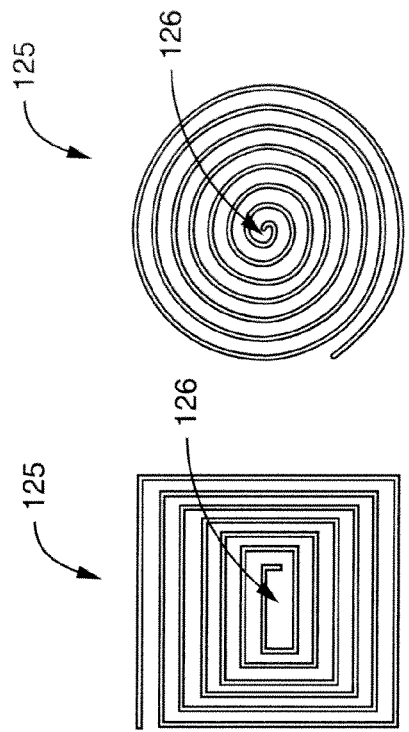
FIGS. 10A and 10B are examples of inductors according to one aspect of the disclosure that can be used in the sensor array of FIG. 9.
Figure 9:
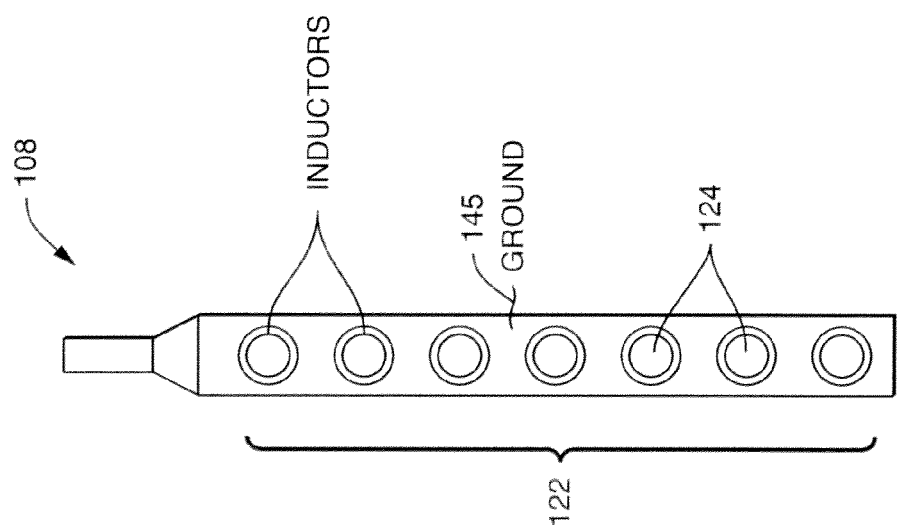
FIG. 9 is an inductor sensor array 108 according to one aspect of the disclosure.

As may be seen in FIGS. 10a and 10b, the induction coils may be of varied shapes, such as round, rectangular or any other shape.

In some instances, it is conceivable that the detection circuit 112 needs to contend with nearby conductive objects that can cause interference. In practical applications, however, such a situation is unlikely because the interference-causing conductive object typically needs to be within one coil diameter of the coil's center 126. This makes the appearance of an interference-causing conductive object unlikely within one coil diameter of the center 126 of the induction coil 125 when the detection circuit 112 is used in conjunction with an absorbent article 20. Nevertheless, an interference problem of this sort can be managed by an intelligent processor that recognizes and stores signal output once the induction coil 125 is in position and activated. The processor uses this signal output as a reference point and interprets subsequent signals in relation to this reference point. In other words, the processor includes an intelligent zeroing feature.

In another aspect of the present disclosure illustrated in the circuit diagram, a grounding plane between the electrical common of the inductor array 122 and the absorbent structure 44 can be used to ensure that the signaling device 110 and the liquid in the absorbent structure 44 are at the same potential or voltage. Such a grounding plane can help the detector circuit 112 to be more sensitive to sensing impedance changes in the induction coil 125 as the grounding plane can reduce noise in the system.

In operation, when the absorbent article 20 has received a first insult, a signal from the marginal oscillator circuit 130 rises to a relatively high level while superabsorbent swelling occurs, but then reaches a plateau as liquid is wicked away from the field of view of the induction coil 125. The field of view of the induction coil 125 is the region in which an insult will affect the induction coil 125. Thus, an abrupt rise in the signal output of the marginal oscillator circuit 130 followed by a leveling is expected. In the absence of superabsorbent, the signal would slowly fall in response to wicking. A second insult to the absorbent article 20 produces an abrupt drop in signal since incoming urine is usually less conductive than swollen superabsorbent. After the second insult is complete, the signal begins to rise again, but to values that are higher than those following the first insult, but ultimately followed again by a period of decay if superabsorbent levels are small. When the detector circuit 112 detects an insult, the signaling device 110 provides a signal to the wearer or to the caregiver as described above.

Figure 13:
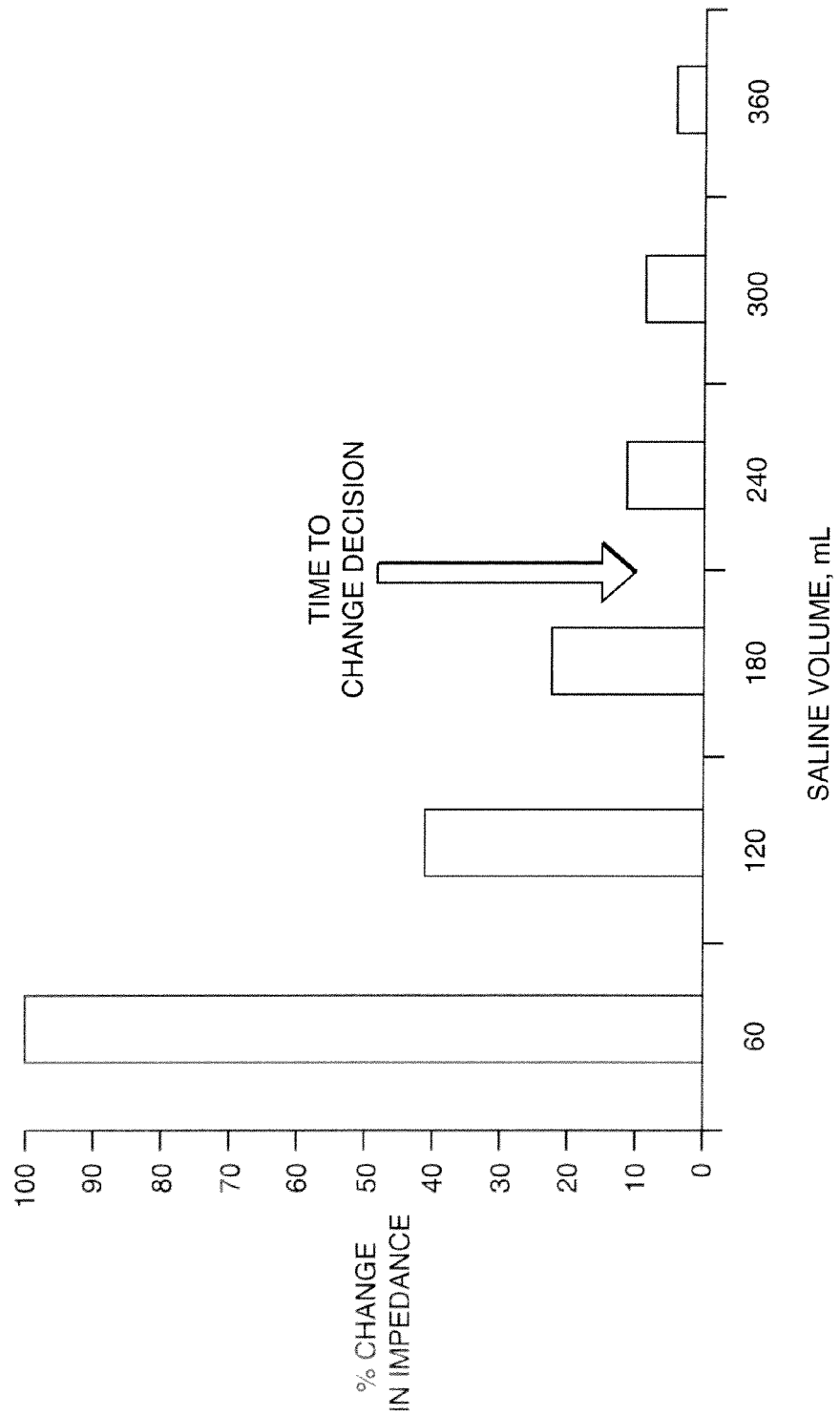
FIG. 13 is a chart showing a normalized variation of impedance according to one aspect of the disclosure.

Data may be obtained through a bench test and mannequin study conducted using saline solution. A 0.9% saline solution is used to create a series of six 60 ml insults having flow rates of 180 ml/min. For each insult, a drop in impedance is occurs. The change in impedance due for each drop is measured. The percent change in impedance for each insult is computed. A chart showing normalized impedance is shown in FIG. 13.

In another aspect of the present disclosure, the capacitance of the monitoring area 128 of the absorbent article 20 is measured. Thus, the sensor array 108 is constructed not with inductive coils 125, but with capacitors 148.

Figure 8B:
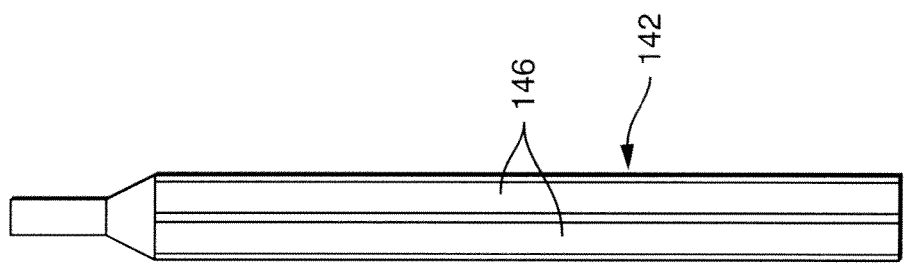
FIGS. 8A and 8B are examples of sensor electrodes according to one aspect of the disclosure.
Figure 8A:
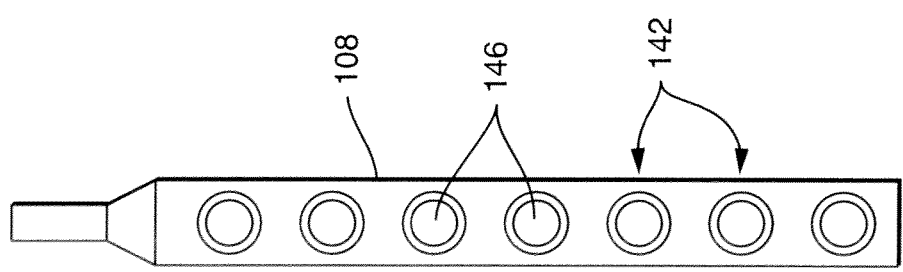

Referring to FIGS. 2 and 8A-8B, the capacitance-based wetness monitoring system 100 senses the fullness of the absorbent article 20. The system 100 includes a sensor array 108 of capacitors 148 which monitors changes in capacitance in response to bodily waste. Due to the higher dielectric permittivity of body waste relative to air, the initial capacitance changes significantly when this type of ionic liquid is within the proximity of the capacitor 148.

Figure 5:
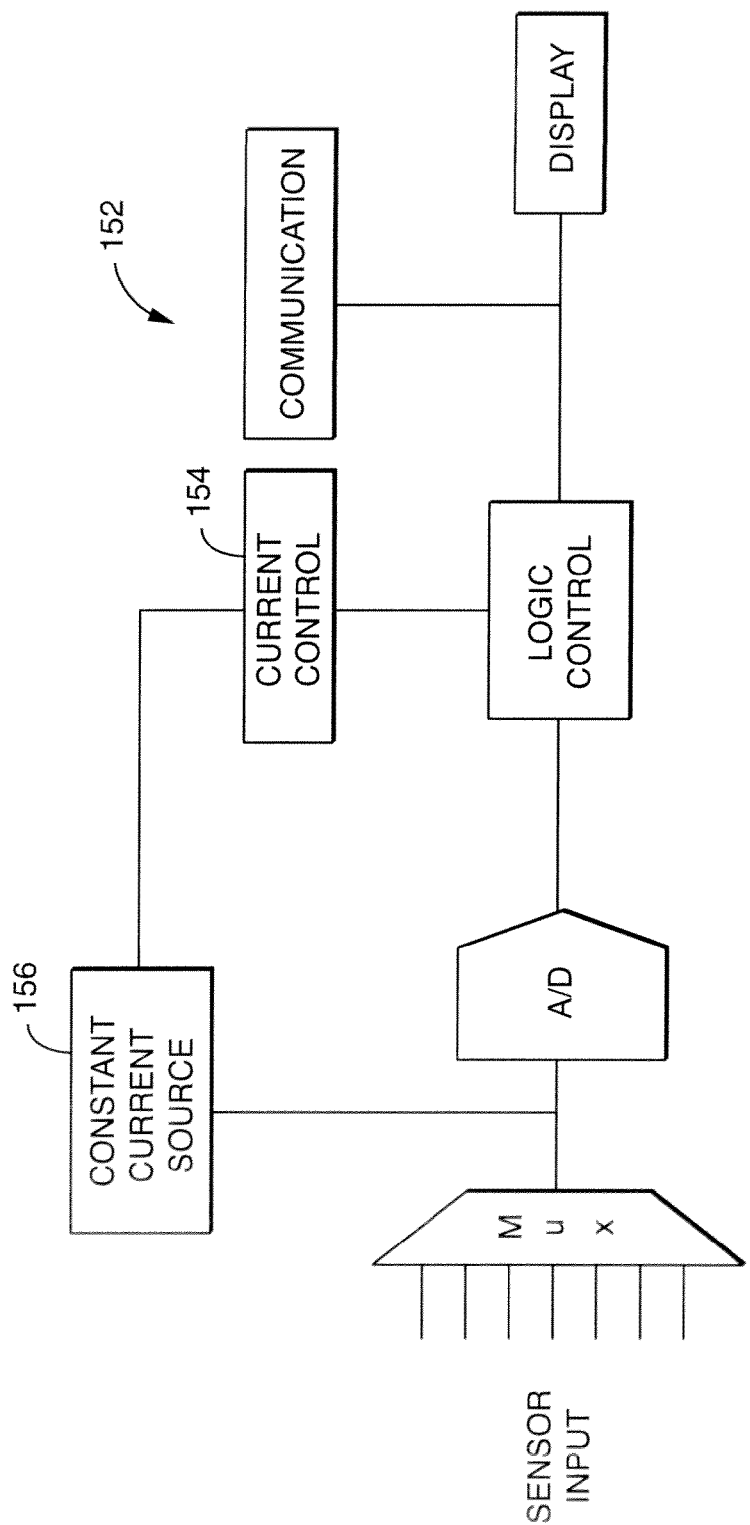
FIG. 5 is a schematic of the signal detection electronics according to one aspect of the disclosure.

Referring to FIGS. 5 and 8A-8B, the electrical signal detection measures changes in the capacitance of the electrode sensor array 108 using a circuit 150. Circuit 150 is optimized to have adequate sensitivity to detect changes in the dielectric permittivity.

In one aspect of the present disclosure best illustrated in FIG. 2, a sensor array 108 includes capacitive sensor(s) 142 adapted to detect the presence of a body exudate in the absorbent article 20. A noninvasive capacitive-based sensor can be used to determine the permittivity of material near the sensing element. In this sense, each capacitive sensor 142 is an open-face virtual capacitor.

The capacitive sensor 142 is defined by electrodes that create an electrostatic field that extends beyond the face of the electrodes. Conductive substances such as body exudates in the absorbent article 20 act as dielectrics that change field dynamics, causing a load on the system. This load amount can be read as merely the presence or the extent of the presence of moisture, for example. Construction and the power applied to the electrodes can control the extent to which the field extends and the frequency of the power can be adjusted to fine tune selectivity to certain dielectrics.

For example, a noninvasive, capacitive sensor 142 can be used to determine the permeability of material near the sensing element. The sensing element can take a form of an inter-digitized electrode forming an open-face virtual capacitor. Similar technology has been used to determine moisture content in soil and in touch sensors such as key pads, thumbwheels, etc. As described herein, this technology can be applied to detect wetness in an absorbent article 20 from outside the outer cover 40. A key challenge, however, with such a capacitive sensing system is managing the penetration depth of the electric field. Such a challenge can be resolved through signal conditioning and developing algorithms to ignore environmental interferences.

Sensor design is important in determining the sensitivity of the capacitive sensor 142 to detect wetness in the absorbent article 20. Some of the design parameters include the physical aspects of the sensor array 108, for example a sensor array area may be about 0.0004 $cm^2$ to about 0.04 $cm^2$; the number of capacitors in one array, for example may be from about 1 to 10; and the spacing between the capacitor and a ground plane, for example from about 1 mm to about 2.5 mm. The ground plane can be positioned at the back of the sensor to prevent interference from the back side of the sensor, such as by touching the garment-facing side of the sensor array 108.

When an absorbent article 20 or any material with a higher dielectric than air is against the capacitive sensor 142, the electrostatic fields present when air was only present now spread into the higher dielectric material and have a better path to a lower potential or ground. This increases the capacitance and can be detected using the system 100. This change may be verified using a bench method standard for such measurement, such as by using a BK Precision LCR Meter. When water is present in the absorbent article 20, the dielectric constant increases much more than when the absorbent article 20 is dry or another dielectric is present. Water has a dielectric greater than 50 and provides a better path for the electric fields to a lower potential or ground.

One aspect of a capacitor system design includes a microcontroller made by Microchip Technologies Inc. of Chandler, Ariz. U.S.A, part number PIC24FJ128GA106, which has a dedicated charge time measurement unit (CTMU). The CTMU is a module add-on to the microcontroller that can be used directly to detect changes in capacitance. In this system design, an array of capacitor sensors are attached to the A/D inputs of the Microchip PIC 24FJ series microcontroller and used to compute the changes in capacitance as the dielectric changes in presence of wetness.

In another aspect, changes are detected in the resonant frequency of an LC circuit. As the capacitance value of the resonator circuit changes the frequency of the oscillating frequency of the resonator changes, this can be detected by a frequency-to-voltage (F/V) converting chip such as TC 9400 made by Microchip Technologies Inc. The F/V converter produces a voltage used by a microcontroller. When a voltage set point is reached, as determined by the microcontroller, an alarm signal is generated as further described herein. A block diagram of such a system is illustrated in FIG. 5.

Yet another aspect measures the time taken to discharge a capacitor. A resistor-capacitor (RC) circuit has a characteristic discharge curve dependent on the capacitor under test. A system capable of measuring the time constant of this discharge curve can be used to detect the changes in the capacitance. In other words, as the capacitance of the system is different with an insulted absorbent article as compared to a dry absorbent article, the discharge curve will be different as well. In use, an open face virtual capacitor is manufactured using an RC circuit including a step function/pulse generator. The discharge time of the system capacitance is detected and processed using a digital signal processing (DSP) algorithm in a microcontroller. When insult occurs, as determined by the microcontroller, an alarm signal is generated as described herein.

As with the inductive sensor, the electronics associated with the capacitive detection circuit 112 are relatively simple and can be miniaturized.

In one aspect, the system can be configured such that the signaling device 110 will not emit signals within a certain period of time once the system 100 is first activated, where being activated means the system 100 is in a condition to detect and provide a signal. The period of time can vary depending upon the particular circumstances and the particular application. For example, in one aspect, the system can be configured not to emit signals for at least the first 15 minutes, such as at least the first 30 minutes, such as at least the first 45 minutes, such as at least the first hour the absorbent article 20 is worn.

In an alternative aspect, steady state is determined by the capacitive detection circuit 112 used in the system 100. Steady state can be determined when substantial or significant changes in capacitance fail to occur for a certain period of time indicating that steady state conditions have been reached. For instance, the system can be configured to only become activated once the capacitive detection circuit 112 determines no substantial changes within the interior of the article 20 for a period of about five minutes, such as about 10 minutes, such as about 20 minutes, such as about 30 minutes, such as about 45 minutes, such as about one hour. For example, if the sensor is a capacitive detection circuit 112, steady state can be determined when the capacitive detection circuit 112 senses no more than about 5 percent change in capacitance on the interior of the article 20 for a period of at least 10 minutes.

When using a capacitive sensor array 108, the sensor array 108 can be placed in any suitable location on the absorbent article 20. For instance, the sensor array 108 can be placed in the crotch region 26, on the back region 24, or on the front region 22 of the article 20 depending upon various factors. The sensor array 108 has a continuous length such that it may extend from one such region to another.

Like the inductive sensor array 122, the capacitive sensor array 108 may be configured to be removed from the absorbent article 20 when the absorbent article 20 is disposed and placed on a new absorbent article 20. In one aspect, the detection circuit 112 and/or signaling device 110 can include multiple settings depending upon the absorbent article 20 to which it is attached. In this manner, the signaling system can be modified based upon the particular product specifications. The product purchased can provide information to the consumer as to which setting to use.

In some instances, it is conceivable that the capacitive detection circuit 112 needs to contend with nearby objects that can cause interference. In practical applications, however, such a situation is unlikely because the interference-causing object typically needs to be very close to the capacitive detection circuit 112. As with the inductive detection circuit, an interference problem of this sort can be managed by an intelligent algorithm that recognizes and stores signal output once the capacitive detection circuit 112 is in position and activated. The algorithm uses this signal output as a reference point and interprets subsequent signals in relation to this reference point. In other words, the algorithm includes an intelligent zeroing feature.

The time-to-change decision is based on two different protocols; one reading total capacitance of the sensor array 108, and the other reading capacitance of individual capacitors 148. One may measure both and determine The time-to-change signal will be generated if any of the measured values are above a pre-determined threshold level.

Figure 7:
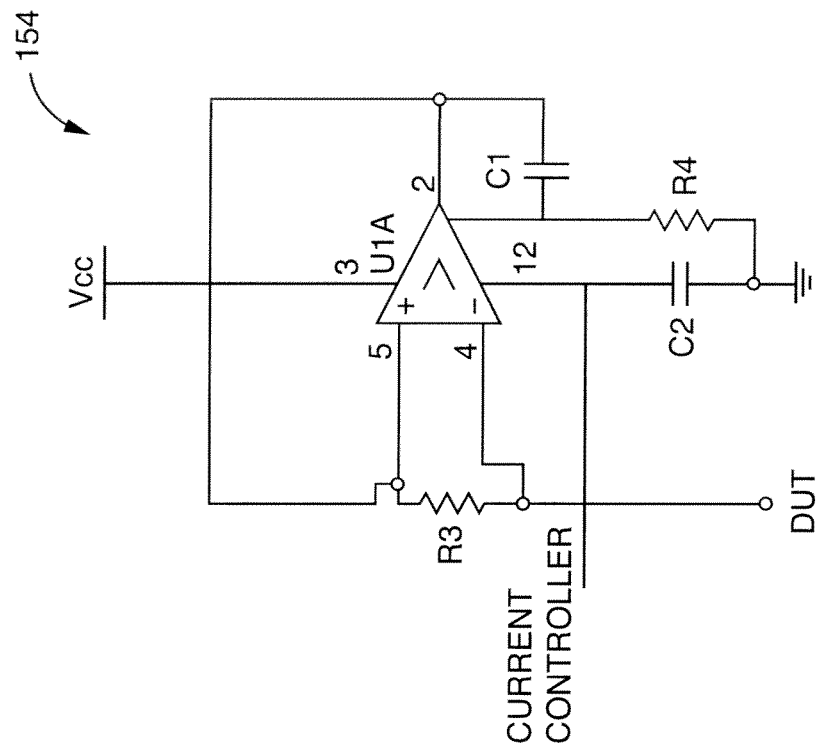
FIG. 7 is a schematic of a constant current controller according to one aspect of the disclosure.
Figure 6:
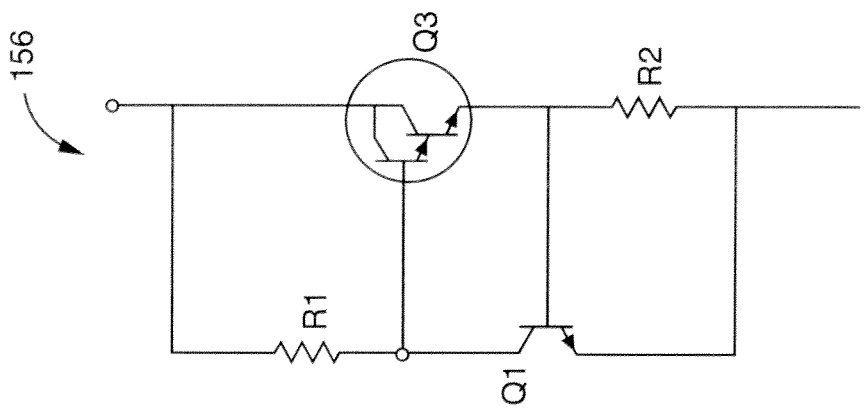
FIG. 6 is a schematic of a constant current source equivalent circuit according to one aspect of the disclosure.

Referring to FIG. 5, which incorporates the circuits of FIGS. 6 and 7, the capacitance change is measured using a charge-discharge circuit 152. The change in capacitance is correlated with the insult amount.

Bench tests and mannequin studies were conducted as previously described. FIG. 13 shows the normalized changes in measured percent change in impedance for the six insults. As can be seen, the percent change in impedance for a second insult drastically changes from that of the first insult. However, the change becomes smaller and smaller for further insults. The variation of impedance is reduced for consecutive insults due to the approaching saturation of the absorbent article 20.

Figure 14:
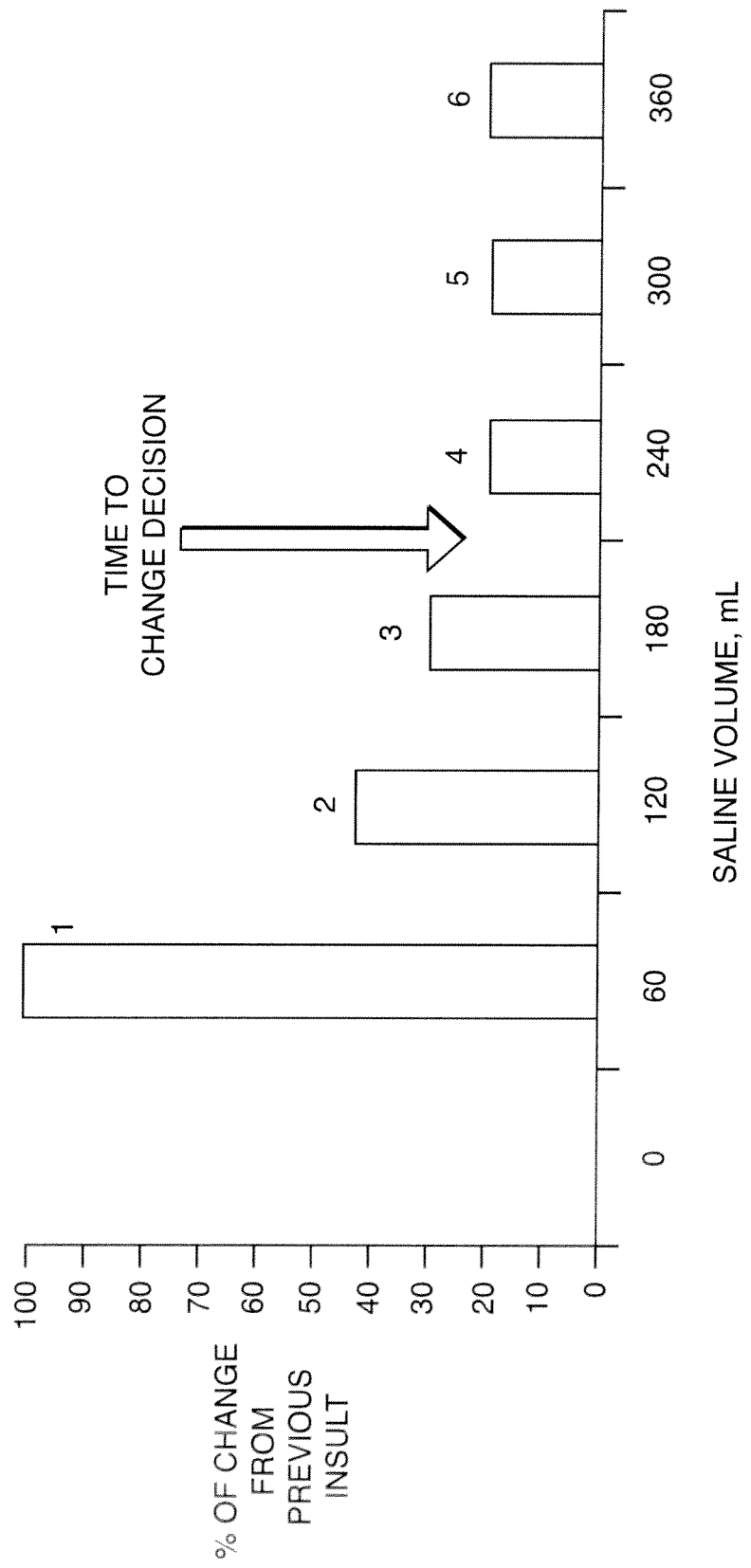
FIG. 14 is a chart showing normalized variation of capacitance according to one aspect of the disclosure.

Likewise, FIG. 14 shows the normalized changes in measured capacitance for the six insults. As can be seen, the capacitance for a second insult drastically changes from that of the first insult. However, the change becomes smaller and smaller for further insults. The variation of capacitance is reduced for consecutive insults due to the approaching saturation of the absorbent article 20.

Regardless of whether the detection circuit employs capacitors or inductors to detect the electrical changes associated with an insulted absorbent article 20, the time-to-change decision is based on an algorithm shown in FIGS. 15 and 16. In one aspect, the time to change decision will be made if the difference in a measured electrical property is less than or equal to 10% of the previous value, or other percentages as desired. For instance, a user may provide input to the signaling device 110 indicating a desired percentage of fullness. Some examples of desired percentages include 50% fullness, 75% fullness, 90% fullness and 100% fullness. In one aspect, the user may be given a range of choices between certain levels of fullness, and may select his or her choice through a signaling device interface (not shown) such as a dial, button or switch that is electrically connected to the signaling device circuitry. In another aspect, the user may similarly provide additional or optional input to the signaling device 110 to select a time to change based on the number of insults that has occurred or the amount of time that has elapsed since a first insult.

Referring to FIG. 15, one possible algorithm for using capacitance readings to determine a time to change is used. The time-to-change decision is made if the difference of a measured value is less than or equal to a predefined threshold value. The algorithm includes the following steps:
1. Activate system 100 by powering the signaling device 110.
2. At time T1, read the total capacitance for the sum of the present sensors in sensor array 108.
3. At time T2 (for example 15 minutes), calculate the average capacitance of the sensor array.
4. Calculate the delta between the T1 moving average baseline capacitance and the T2 average capacitance.
   a. If the delta is below a threshold value, a time to change signal is delivered to the user by enabling an output to a user.
   b. If the delta is above the threshold value, the average moving baseline equals the last average capacitance. Steps 3 and 4 are repeated.

Referring to FIG. 16, an algorithm for using inductance readings to determine time to change is used. The time-to-change decision is made if the difference of in a measured value is less than or equal to a predefined threshold value. The algorithm includes the following steps:
1. Activate system 101 by powering the signaling device 110.
2. At time T1, determine if there is any conductivity due the presence of moisture in the absorbent structure 44.
   a. If the absorbent structure 44 is not conductive, repeat step 2 at time T2.
   b. If the absorbent structure 44 is conductive, calculate a moving average baseline impedance Z.
3. Calculate the delta between the T1 moving average baseline impedance Z and the T2 average impedance.
   a. If the delta is below a threshold value, a time-to-change signal is delivered to the user by enabling an output to the user.
   b. If the delta is above the threshold value, the average moving baseline equals the last average impedance, and time T1 equals Tn. Steps 2 and 3 are repeated.

The absorbent article 20 including the sensor array 108 is donned by a wearer. The user may adjust the signal processing circuit to predetermined threshold level on which the time to change decision will be made. The user attaches the signaling device 110 to the absorbent article 20. When the signaling device provides a signal, the user will know that the absorbent article has reached the predetermined threshold that corresponds either to a level of fullness of the absorbent structure 44, and/or a certain amount of lapsed time and/or a desired number of insults.

Another aspect of the disclosure is a wetness detection kit. The kit includes the system 100 and a plurality of absorbent articles (e.g. diapers). The system 100 may be semi-disposable wherein a power supply is built into the system 100 such that it is not replaceable, or the system 100 may have a replaceable power supply so that it may conceivably be used for a person's entire duration of a need to use of the absorbent article, such as the many months a baby wears a diaper. As described previously the system 100 senses and indicates the presence of a body exudate in an absorbent article 20. The system 100 includes a signaling device 100 having a housing 114 and a detection circuit 112, and a sensor array 108 electrically connected to the detection circuit 112. The sensor array includes a plurality of sensors disposed on an elongated substrate. The system 100 may be sequentially and removably attached to each one of the plurality of absorbent articles. It is contemplated that a system 100 may by packaged with a 20, 30, 40, or 50 count of absorbent articles, so that a user may removably attach the system 100 to each of the absorbent articles in the package.

Aspects of the disclosure have been described with reference to various specific and illustrative aspects and techniques. However, it should be understood that many variations and modifications may be made while remaining within the spirit and scope. Accordingly, this is intended to embrace all such alternatives, modifications and variations that fall within the spirit and scope of the appended claims. As various changes could be made in the above constructions and methods, without departing from the scope of the disclosure, it is intended that all matter contained in the above description and shown in the accompanying drawings shall be interpreted as illustrative and not in a limiting sense.

When introducing elements of the disclosure or the preferred aspect(s) thereof, the articles "a", "an", "the" and "said" are intended to mean that there are one or more of the elements. The terms "comprising," "including," and "having" are intended to be inclusive and mean that there may be additional elements other than the listed elements.

The invention claimed is:

1. A system for sensing and indicating the presence of a body exudate in an absorbent article having an absorbent structure, a front region, a crotch region, and an outer cover, the system comprising:
   a signaling device comprising a housing that houses a detection circuit;
   a sensor array electrically connected to the detection circuit, wherein the sensor array comprises a plurality of sensors disposed on a single elongated substrate, and wherein the substrate is configured to extend away from the housing from the front region to the crotch region,
   wherein the plurality of sensors are configured to detect the amount of the body exudate within the absorbent article without making direct contact with the absorbent structure, and wherein the signaling device is configured to provide a signal to a user when a measured value is less than or equal to a predefined threshold value to provide the user with a time-to-change decision.

2. The system of claim 1 wherein the plurality of sensors comprise capacitive sensors.

3. The system of claim 2 wherein the capacitive sensors comprise open-face virtual capacitors.

4. The system of claim 2 wherein the measured value is a delta between a moving average baseline capacitance and an average capacitance.

5. The system of claim 1 wherein the plurality of sensors comprise induction coils.

6. The system of claim 5 wherein the induction coils have a dimension, either the longest axis or a diameter, of 0.5 cm to 3 cm.

7. The system of claim 5 wherein the measured value is a delta between a moving average baseline impedance and an average impedance.

8. The system of claim 1 wherein the signaling device comprises a display of a number of body exudate insults and/or elapsed time from first insult and/or a percentage of absorbent article fullness.

9. The system of claim 8 wherein the signaling device is adapted to provide a visual notification.

10. The system of claim 8 wherein the signaling device is adapted to provide an audible notification.

11. The system of claim 8 wherein the signaling device is adapted to provide a vibratory notification.

12. The system if claim 8 wherein the detection circuit comprises a marginal oscillator circuit.

13. A wetness detection kit comprising:
- a plurality of absorbent articles each having a front region and a crotch region; and
- a system for sensing and indicating the presence of a body exudate in an absorbent article, the system comprising a signaling device comprising a housing and a detection circuit; and
- a sensor array electrically connected to the detection circuit using a single electrical contact, wherein the sensor array comprises a plurality of sensors disposed on a single elongated substrate, wherein the substrate is configured to extend away from the housing from the front region to the crotch region, and wherein the signaling device is configured to provide a signal to a user when a measured value is less than or equal to a predefined threshold value to provide the user with a time-to-change decision;
- wherein the system may be sequentially and removably attached to each one of the plurality of absorbent articles.

14. The wetness detection kit of claim 13 wherein the system further comprises an attachment mechanism for removably attaching the system to one of the plurality of absorbent articles.

15. A body exudate collection and detection system comprising:
- an absorbent article comprising an outer cover, a front region, a crotch region, and a longitudinal axis; and
- a signaling device comprising a housing and a detection circuit; and a sensor array electrically connected to the detection circuit by a single contact and partially housed by the housing; wherein the sensor array comprises a plurality of sensors disposed on a single elongated substrate, and wherein the substrate is configured to extend away from the housing along the longitudinal axis from the front region to the crotch region;
- wherein the signaling device is attached to the outer cover and is configured to provide a signal to a user when a measured value is less than or equal to a predefined threshold value to provide the user with a time-to-change decision.

16. The system of claim 15 wherein the sensor array is oriented parallel to the longitudinal axis.

17. The system of claim 16 wherein the absorbent article further comprises a front region, a crotch region and a back region, and the sensor array has a continuous length such that it extends from the front region to the back region.

18. The system of claim 15 wherein the signaling device comprises a display of a number of body exudate insults.

19. The system of claim 15 wherein the signaling device comprises a display of elapsed time.

20. The system of claim 15 wherein the signaling device comprises a display of the percentage of fullness.

21. The system of claim 15 wherein the sensor array comprises an electronic ground plane located on a substrate surface of the sensor array that is oriented toward the outer surface.

* * * * *